(12) United States Patent
Larsson et al.

(10) Patent No.: US 8,632,883 B2
(45) Date of Patent: Jan. 21, 2014

(54) SEPARATION MEDIA FOR BIOMOLECULES COMPRISING POROUS HYBRID PARTICLES CONTAINING INORGANIC METAL OXIDE NANOPARTICLES

(75) Inventors: Anders Larsson, Uppsala (SE); Ulrika Meyer, Uppsala (SE); Nils Norrman, Uppsala (SE); Johan Ohman, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 368 days.

(21) Appl. No.: 12/864,070

(22) PCT Filed: Feb. 12, 2009

(86) PCT No.: PCT/SE2009/000083
§ 371 (c)(1),
(2), (4) Date: Jul. 22, 2010

(87) PCT Pub. No.: WO2009/102258
PCT Pub. Date: Aug. 20, 2009

(65) Prior Publication Data
US 2010/0294977 A1    Nov. 25, 2010

(30) Foreign Application Priority Data
Feb. 15, 2008    (SE) ...................... 0800354

(51) Int. Cl.
*B32B 5/16* (2006.01)
*C08J 9/35* (2006.01)
*C08L 5/00* (2006.01)
*C08L 5/02* (2006.01)

(52) U.S. Cl.
USPC ........... 428/402; 428/403; 428/407; 523/218; 523/333; 523/447; 523/448

(58) Field of Classification Search
CPC ................ C08J 9/35; C08L 5/00; C08L 5/02; B32B 5/16
USPC ........... 428/402–407; 523/218, 333, 447, 448
See application file for complete search history.

(56) References Cited

U.S. PATENT DOCUMENTS 4,489,174 A * 12/1984 Karickhoff ...................... 521/54
5,834,121 A    11/1998 Sucholeiki et al.
(Continued)

FOREIGN PATENT DOCUMENTS

EP    1 477 800    11/2004
EP    1 165 201    2/2007
(Continued)

OTHER PUBLICATIONS

Pasqui et al., Chemical and biological properties of polysaccharide-coated titania nanoparticles: The key role of proteins, Biomacromolecules, 12, 1243-1249 (2011) [dx.doi.org/10.1021/bm101521e].*

(Continued)

*Primary Examiner* — Hoa (Holly) Le

(57) ABSTRACT

The present invention relates to separation of biomolecules. More closely, the invention relates to a method for production of a separation medium comprising hybrid particles of inorganic and organic material as well as the hybrid particles produced by this method. Finally, the invention relates to use of the hybrid particles for separation of biomolecules, preferably phosphoproteins. The method comprises the following steps: addition of inorganic metal oxide particles to an organic solution to form a mixture; and emulsification of the mixture to form porous hybrid particles, wherein the density of the porous hybrid particles is between 1.0 and 1.5 g/ml, and wherein the inorganic particles have a shape and size that maximizes their active surface area enabling the inorganic particles to interact with biomolecules.

25 Claims, 1 Drawing Sheet

A   B   C

Organic solution mixed with inorganic particles   Emulsification followed by gelation or polymerisation   Porous hybrid particles

(56) References Cited

U.S. PATENT DOCUMENTS

| | | | |
|---|---|---|---|
| 5,837,049 A * | 11/1998 | Watson et al. | 106/427 |
| 5,837,826 A * | 11/1998 | Flickinger et al. | 530/413 |
| 5,866,006 A * | 2/1999 | Lihme et al. | 210/635 |
| 6,613,234 B2 * | 9/2003 | Voute et al. | 210/656 |
| 6,984,733 B2 * | 1/2006 | Berg et al. | 536/124 |
| 2006/0025585 A1 * | 2/2006 | Berg et al. | 536/124 |
| 2007/0181038 A1 * | 8/2007 | Sabesan et al. | 106/501.1 |

FOREIGN PATENT DOCUMENTS

| | | |
|---|---|---|
| EP | 1 780 537 | 5/2007 |
| WO | WO 97/17132 | 5/1997 |
| WO | WO 99/51316 | 10/1999 |
| WO | WO 99/51335 | 10/1999 |
| WO | 2009/102258 * | 8/2009 |

OTHER PUBLICATIONS

Kweon, H., et al., Analytical Chemistry, (2006), 78(6):1743-1749.

Larsen, M., et al., Molecular and Cellular Proteomics, (2005), 4:873-886.

Larsen, M., et al., Molecular and Cellular Proteomics, (2007), 6.10:1778-1787.

Rhodes, M., Introduction to Particle Technology, (1998), 55-72.

Zhou, H., et al., Electrophoresis, (2007), 28:2201-2215.

* cited by examiner

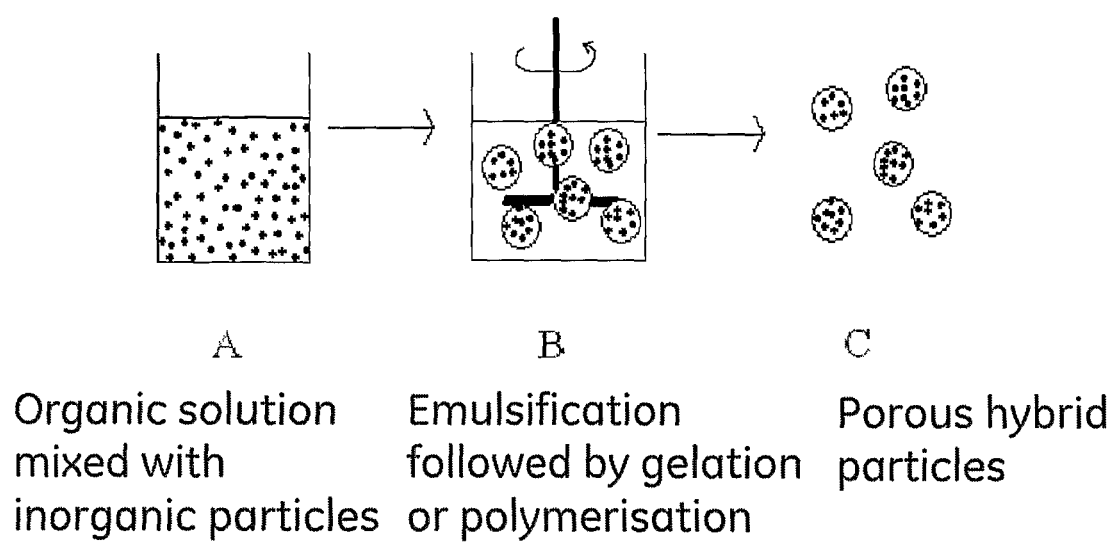

SEPARATION MEDIA FOR BIOMOLECULES COMPRISING POROUS HYBRID PARTICLES CONTAINING INORGANIC METAL OXIDE NANOPARTICLES

CROSS-REFERENCE TO RELATED APPLICATIONS

This application is a filing under 35 U.S.C. §371 and claims priority to international patent application number PCT/SE2009/000083 filed Feb. 12, 2009, published on Aug. 20, 2009, as WO 2009/102258, which claims priority to patent application number 0800354-3 filed in Sweden on Feb. 15, 2008.

FIELD OF THE INVENTION

The present invention relates to separation of biomolecules. More closely, the invention relates to a method for production of a separation medium comprising hybrid particles of inorganic and organic material as well as the hybrid particles produced by this method. Finally, the invention relates to use of said hybrid particles for separation of biomolecules, preferably phosphoproteins.

BACKGROUND OF THE INVENTION

There are various known interactions between biomolecules and inorganic material, for example electrostatic interactions, used e.g. in ion exchange chromatography, hydrophobic interactions, used e.g. in hydrophobic interaction chromatography and reversed phase chromatography, pi electron interactions. Also, in affinity chromatography, highly specific and geometrically defined combinations of several interactions are used to obtain very high specificities.

Phosphorylation is a reversible post-translational modification in eukaryotes. Phosphorylation occurs either by addition or by removal of a phosphate group in a protein. Kinases are responsible for the addition of phosphate to a protein while phosphatases are responsible for the removal of phosphate from a protein. The function of these post-translational modifications is to alter the substrate's activity, subcellular localization, binding properties or association with other proteins. Many enzymes and receptors acts like an on-off switch when phosphorylated. This means that enzymes and receptors are activated or deactivated by phosphorylation. An important feature of kinases and phosphatases is that a single molecule is able to activate many substrate molecules, thus allowing for amplification of the initial signal. Both kinases and phosphates are interesting because all signal transduction pathways are regulated, on some level, by phosphorylation, making phosphorylation relevant to most, if not all, areas of cell signalling and neuroscience research. Furthermore, phosphorylation plays an important role in cancer diseases, inflammatory diseases, metabolic disorders and neurological diseases.

To enrich phosphopeptides for example IMAC (Immobilized metal ion affinity chromatography) or MOAC (metal oxide/hydroxide affinity chromatography) may be used.

Recently, titanium dioxide was reported useful for isolation of phosphopeptides (Martin R. Larsen, Tine E. Thingholm, Ole N. Jensen, Peter Roepstorff, and Thomas J. D. Jorgensen. Highly Selective Enrichment of Phosphorylated Peptides from Peptide Mixtures Using Titanium Dioxide Microcolumns Molecular & Cellular Proteomics 4.7 p. 873-886). For enrichment of phosphopeptides zirconium dioxide has also reported useful (Kweon, H. K. and Håkansson, K. Selective Zirconium Dioxide-Based Enrichment of Phosphorylated peptides for Mass Spectrometric Analysis. Anal. Chem. 2006, 78, 1743-1749).

Another common post-translational modification of proteins is glycosylation. Glycosylation is an enzyme directed site-specific process of attaching saccharides to proteins. The donor molecule is a nucleotide sugar. The glycosylation is of importance for the protein folding, for the cell-cell adhesion as well as for the immune system. For many diseases like cancer the protein glycosylation pattern is affected. Therefore the glycosylated proteins are being studied as biomarkers used for diagnosis and follow-up of certain unhealthy conditions. The sialiome, sialic acid-containing glycopeptides, was characterized using titanium dioxide as an enrichment step in a report from Martin R Larsen, Soren S. Jensen, Leene A. Jakobsen, and Niels H. H. Heegard. Exploring the Sialiome Using Titanium Dioxide Chromatography and Mass Spectrometry. Molecular & Cellular Proteomics 6.10 p 1778-1787.

EP1477800 describes a method and apparatus for analyzing phosphoproteins using a reversed phase HPLC column having a titanium dioxide pre-treatment column.

EP1780537 describes the purification of phosphorylated proteins on an immobilized metal or titania carrier wherein a solution containing acetonitrile is used.

EP 1165201 relates to particulate material for fluidised bed purification of bio-macromolecules. The particles are essentially construed of a polymeric base matrix, e.g. a polysaccharide such as agarose, and a non-porous core material, e.g. steel and titanium. The purpose of the core material is to give the particulate material a density above 2.5 g/ml.

SUMMARY OF THE INVENTION

The present invention relates to a novel separation medium comprising porous hybrid particles capable of interacting with specific biomolecules.

In a first aspect the invention relates to a method for production of separation media for separation of biomolecules from a sample, comprising the following steps addition of inorganic metal oxide particles to an organic solution to form a mixture; and emulsification of said mixture to form porous hybrid particles, wherein the density of said porous hybrid particles is between 1.0 and 1.5 g/ml, and wherein said inorganic particles have a shape and size that maximizes their active surface area enabling said inorganic particles to efficiently interact with biomolecules. In this way the inorganic metal oxide particles are accessible for binding of proteinaceous and peptide material.

The inorganic particles should have a shape and size that maximizes their active surface area. For example, the inorganic particles may be porous and/or small. Preferably the inorganic particles are small, namely less than 1000 nm, preferably less than 300 nm, in size. These small particles can either be individually dispersed or can be used in the form of aggregates made up from small primary particles.

The inorganic particles may be selected from Group 4, 12, 13 and/or 14 and are preferably titania, zirconia, hafnia, alumina, zinc oxide, germania and/or tin dioxide, preferably titania, zirconia and/or alumina, most preferably titania.

The organic particles solution comprises polysaccharides, for example agarose or dextran.

Alternatively, the organic solution comprises synthetic material, for example, polystyrene/dvb and porogens or methacrylates and porogens.

In a preferred embodiment of the method according to the present invention inorganic particles are added to the disperse phase in suspension gelation/polymerisation of porous beads. During emulsification the inorganic particles will be incorporated in the organic porous phase.

In a further embodiment the hybrid particles might be synthesised in a fashion that adds superparamagnetic properties to the hybrid particles. For example magnetite may be added together with the inorganic particles in the dispersed solution made for emulsification. The magnetic format is advantageous since it is very easy to handle in the small scale sample preparation mode.

In a second aspect, the invention relates to porous hybrid particles comprising inorganic metal oxide particles selected from Group 4, 12, 13 and/or 14 which are incorporated in organic solution to form porous hybrid particles, wherein the density of the hybrid particles is between 1.0 and 1.5 g/ml, preferably between 1.0 and 1.3 g/ml, and wherein said inorganic particles have a shape/size that maximizes their active surface area and said inorganic particles are capable of interacting with biomolecules. The incorporation is made in such a way that the inorganic particles are active and available for protein and peptide binding. The hybrid particles are preferably in the form of porous beads.

The inorganic particles have a (volume-weighted, sphere volume-equivalent) average diameter of 10 to 1000 nm, preferably 10-300 nm If aggregated particles are used, the primary particles in the aggregates have an average diameter of 10 to 1000 nm, preferably 10-300 nm. For a description of methods to determine average particle diameters, see e.g. M Rhodes: Introduction to particle technology, Wiley 1998, pp 55-72. For a discussion about determination of primary particle sizes in aggregated particles, see Degussa technical bulletin pigments no 60, Significance and existence of primary particles in highly dispersed materials $2^{nd}$ Ed. 1986. This reference (p 7) also describes the inverse proportionality between particle size and specific surface area.

Preferably the inorganic particles are selected from titania, zirconia, hafnia, alumina, zinc oxide, germania and/or tin dioxide, preferably titania, zirconia and/or alumina, most preferably titania.

Preferably the organic porous material is selected from polysaccharides or synthetic polymers.

In a preferred embodiment the inorganic particles comprise titania and the organic particles comprise agarose, wherein the titania particles are dispersed into the agarose.

Preferably, the size of the hybrid particles is 5-500 μm, preferably 25-100 μm.

In a further embodiment the porous hybrid particles comprise a lid covering the hybrid particles, wherein said lid comprises up to 20% agarose. It is possible to vary the amount of agarose in the porous beads to exclude different sizes of biomolecules from interaction with the active part, i.e. the inorganic material, of the porous beads. For example, large phosphoproteins may be excluded from interaction and elute in the flow through if the separation medium of the invention is used in a chromatographic mode. The medium of the invention is not restricted to chromatography but may also used in other formats, preferably small scale formats, for example high throughput plates, magnetic centrifugation and spin trap columns.

In a third aspect, the invention relates to use of the porous hybrid particles in the purpose of separation, purification or enrichment of biomolecules, such as phosphoproteins or -peptides or glycoproteins or -peptides.

BRIEF DESCRIPTION OF THE DRAWINGS

FIG. 1A shows inorganic metal oxide particles (illustrated by filled squares) dispersed in organic polymer/monomer solution.

FIG. 1B shows the formation of emulsification droplets containing the dispersed inorganic particles followed by gelation or polymerisation.

FIG. 1C is the resulting porous organic/inorganic hybrid particles.

DETAILED DESCRIPTION OF THE INVENTION

The invention relates to porous hybrid particles comprising inorganic and organic material. Preferentially the inorganic material is particles having a large active surface area, meaning that they should either be small (below 1000 nm primary particle diameter, preferably below 300 nm) or that they should be porous. It is preferred that they are small and nonporous due to mass transport, availability and ease of manufacture reasons. For example, pigment-grade titanium dioxide particles are readily available in the desired particle size range and can be used, provided that the particles show a pure titanium dioxide surface (many $TiO_2$ pigments are surface treated with other oxides or with organic material). Porous hybrid particles made from polysaccharide may be used directly without hydrophilisation for the intended application while porous hybrid particles based on for example; polystyrene/dvb or methacrylates need hydrophilisation before use for separation of biomolecules. Hydrophilisation might be done using for example radical grafting using DEGVE, sorbitol coupling or dextran modification.

The amount of inorganic particles should be high enough to give a large available surface but not so high that the density of the hybrid beads is increased above 1.5 g/ml, preferably not above 1.2, causing difficulties in handling and in column packing.

Preferably the organic particles are made of agarose. Agarose has an ability to assemble itself in complex bundles to form gels in aqueous solution when cooling. Agarose dissolved in warm water can be emulsified in for example toluene, thus forming small droplets in the toluene-phase. Upon cooling below the gelling temperature the small droplets of water dissolved agarose forms a spherical, porous gel built from agarose bundles. The size of these particles can be altered using different stirring rates.

In a preferred embodiment of the present invention, small titanium dioxide particles were mixed with the hot agarose water phase. The agarose/titanium slurry was emulsified into toluene. The inorganic particles are physically caught in the bundles or in the porosity of the particle. Epichlorohydrin was used to fixate the agarose structure by means of crosslinking.

EXAMPLES

The present examples are provided for illustrative purposes only, and should not be construed as limiting the scope of the present invention as defined by the appended claims. All references given below and elsewhere in the present specification are hereby included herein by reference.

Experiment 1

Screening of Commercial Inorganic Particles on Distribution in Agarose Gel

A screening experiment was carried out to identify the inorganic particles having the best distribution in agarose gel. The distribution of inorganic particles in agarose gel was evaluated in a thin film format. The commercial inorganic particles listed in Table 1 were included in this experiment.

TABLE 1

The properties of seven different commercial inorganic particles.

| Commercial name | Supplier | Material | Crystal Phase | Size | Surface area (m²/g) | Comment |
|---|---|---|---|---|---|---|
| Kemira AFDC | Kemira Pigments Oy, Pori, Finland | $TiO_2$ | Anatase | Crystal size ~170 nm | 10 | Uncoated |
| UV-Titan M111 | Kemira Pigments Oy, Pori Finland | $TiO_2$, Alumina | Rutile | Crystal size ~14 nm | 100 | Alumina treated |
| FINNTi X-141 | Kemira Pigments Oy, Pori Finland | $TiO_2$, Titanium hydroxide | Anatase | Particle size 1-2 μm | 250-350 | titanium hydroxide and titanium dioxide |
| VP $TiO_2$ P90 | Degussa GmbH | $TiO_2$ | — | Average primary particle size approx 14 nm | 90 ± 20 | — |
| Titanium oxide T815 | Chemat Technology Inc., Northridge, CA | $TiO_2$ colloidal in water | — | Particle size 20-50 nm | — | Colloidal in water |
| VP Zirkonium oxide PH | Degussa Frankfurt/Main, Germany | $ZrO_2$ | — | — | 40 ± 15 | — |
| VP Zirkonium oxide 3-YSZ | Degussa Frankfurt/Main, Germany | $ZrO_2$, yttrium oxide | — | Average primary particle size <30 nm | 40 ± 15 | 3 mol % yttrium oxide |

A 4 w % agarose solution was prepared taking into consideration that the agarose raw material contains 8.3% water and 0.44% ash. The amount pure agarose was calculated with Formula 1 (assuming the density of water 1.0 g/ml) and the quantity of agarose raw material was calculated using Formula 2.

$$\frac{X}{(X+25)} = 0,04 \rightarrow X = 1,053 \quad \text{Formula 1}$$

$$X = \text{Weight(g) pure agarose}$$

$$Y = 1,053 + 0,083Y + 0,0044Y \rightarrow Y = 1,1538 \quad \text{Formula 2}$$

$$Y = \text{Weight(g) crude agarose}$$

Agarose, water and inorganic particles were mixed in round bottom flasks. The flasks were placed in an oil bath and during stirring heated to approximately 95° C. for 4 hours. Thereafter the temperature of the oil bath was decreased to 55° C. 5-10 ml agarose/titanium dioxide mixture was placed on a warm preheated glass plate and then cast using an adjustable film applicator with a unit gap of 1 mm The resulting agarose films were studied by optical light microscope to evaluate the distribution of inorganic particles and aggregate formation in the agarose gel matrix.

FINNTI X-141 showed an even distribution in agarose with no aggregates formed. VP TiO2 PV90, Kemira AFDC and VP Zirkonoxid 3-YSZ showed some small aggregate formation. UV-Titan MIII and VP Zirkonoxid PH had formed large aggregates. The Titanium oxide T815 gave discoloration and the agarose mixture did not gel upon cooling. The VP TiO2 PV90, Kemira AFDC, UV-Titan MIII and FINNTI X-141 were chosen for further experiments.

Experiment 2

Synthesis of Porous Agarose/Inorganic Hybrid Particles Using Different Amounts of Inorganic Particles This experiment was performed with different amounts of inorganic particles of FINNTI X-141.

4 w % agarose in water was mixed with inorganic particles (Table 2) and placed in a round bottom flask equipped with mechanical stirring. The slurry was heated in an oil bath tempered at 100° C. for 4 hours.

In parallel, a solution of 3 g ethyl cellulose in 50 ml toluene was prepared in a jacketed reactor. A circulation bath was connected to the reactor and set to a temperature of 60° C. A glass stirrer was used to mix and solve the ethyl cellulose with the toluene.

When the temperature reached 60° C., 5-10 ml agarose/inorganic solution was added to the toluene phase in the reactor. The stirring rate was stepwise increased during emulsification and the emulsion was allowed to equilibrate for at least 10 min at each stirring rate. After each step a sample was withdrawn and the size of the agarose/inorganic particles was estimated using an optical light microscope. When the mean particle diameter was estimated to less then 100 μm the emulsification process was stopped by cooling the reactor to 5° C. by adding ice to the circulation bath.

The obtained agarose/inorganic particles were slurried in ethanol to remove ethylcellulose and thereafter allowed to sediment. The supernatant was removed. This washing procedure was repeated 3-4 times. Thereafter the agarose/inorganic particles were washed in plenty of water to remove the ethanol.

TABLE 2

Parameters used in Experiment 2

| Exp. No | Commercial name | Inorganic particles (g) | Agarose raw material (g) | Water (ml) | Start stirring rate (rpm) | End stirring rate (rpm) | Calculated density of hybrid particles (g/ml) |
|---|---|---|---|---|---|---|---|
| 2A | FINNTI X-141 | 2.3 | 2.3 | 50 | 130 | 263 | 1.0 |
| 2B | FINNTI X-141 | 2.3 | 2.3 | 50 | 200 | 200 | 1.0 |
| 2C | FINNTI X-141 | 26 | 2.3 | 50 | 200 | 200 | 1.3 |
| 2D | FINNTI X-141 | 78 | 2.3 | 50 | — | — | 1.8 |
| 2E | FINNTI X-141 | 78 | 2.3 | 65 | — | — | 1.7 |
| 2F | FINNTI X-141 | 32 | 2.3 | 50 | 200 | 200 | 1.4 |

The above experiment was performed with different amounts of inorganic particles of FINNTI X-141 resulting in calculated densities from 1.0 to 1.8 g/ml. Particles having a density of 1.4 g/ml or below, were selected for further experiments because they had suitable properties in respect of viscosity.

Experiment 3

Synthesis of Porous Agarose/Inorganic Hybrid Particles Using Different Types of Inorganic Particles Experiment 3 was performed using different types of inorganic particles. 4 w % agarose in water was mixed with inorganic particles (Table 3) and placed in a round bottom flask equipped with mechanical stiffing. The slurry was heated in an oil bath tempered at 100° C. for 4 hours.

In parallel, a solution of 3 g ethyl cellulose in 50 ml toluene was prepared in a jacketed reactor. A circulation bath was connected to the reactor and set to a temperature of 60° C. A glass stirrer was used to mix and solve the ethyl cellulose with the toluene.

When the temperature reached 60° C., 5-10 ml agarose/inorganic solution was added to the toluene phase in the reactor. The stirring rate was stepwise increased during emulsification and the emulsion was allowed to equilibrate for at least 10 min at each stiffing rate. After each step a sample was withdrawn and the size of the agarose/inorganic particles was estimated using an optical light microscope. When the mean particle diameter was estimated to less then 100 µm the emulsification process was stopped by cooling the reactor to 5° C. by adding ice to the circulation bath.

The obtained agarose/inorganic particles were slurried in ethanol to remove ethylcellulose and thereafter allowed to sediment. The supernatant was removed. This washing procedure was repeated 3-4 times. Thereafter the agarose/inorganic particles were washed in plenty of water to remove the ethanol.

TABLE 3

Parameters used in Experiment 3

| Exp. No | Commercial name | Inorganic particles (g) | Agarose raw material (g) | Water (ml) | Start stirring rate (rpm) | End stirring rate (rpm) | Calculated density of hybrid particles (g/ml) |
|---|---|---|---|---|---|---|---|
| 3A | FINNTI X-141 | 26 | 2.3 | 50 | 200 | 200 | 1.3 |
| 3B | Kemira AFDC | 39 | 2.3 | 50 | 200 | 200 | 1.5 |
| 3C | UV-Titan MIII | 44.2 | 3.5 | 75 | 200 | 1000 | 1.4 |
| 3D | VP TiO2 PV90 | 7 | 2.3 | 50 | 230 | 400 | 1.1 |

Experiment 4

Synthesis of Porous Agarose/Inorganic Hybrid Particles

A mixture of 3.7 g agarose and 40 g titanium dioxide Kemira AFDC solved in 80 ml water was placed in a round bottle flask and heated in an oil bath (100° C.) for one hour (approximately 95° C. in the flask).

In parallel, a solution of 14 g ethyl cellulose in 200 ml toluene was prepared in a jacketed reactor. A circulation bath was connected to the reactor and set to a temperature of 60° C. An inpeller was used to mix and solve the ethyl cellulose with the toluene.

When the temperature reached 60° C., the ml agarose/inorganic solution was added to the toluene phase in the reactor. The stirring rate was stepwise increased during emulsification and the emulsion was allowed to equilibrate for at least 5 min at each stirring rate. After each step a sample was withdrawn and the size of the agarose/inorganic particles was estimated using an optical light microscope. When the mean particle diameter was estimated to less then 100 µm the emulsification process was stopped by cooling the reactor to 15° C. by adding ice to the circulation bath.

The obtained agarose/inorganic particles were slurried in ethanol to remove ethylcellulose and thereafter allowed to sediment. The supernatant was removed. This washing procedure was repeated 5 times. To see if the supernatant was removed after 5 washes, some of the supernatant was added to water. If there was a precipitation the ethylcellulose was still present and the agarose/inorganic particles was further washed with ethanol. Thereafter the agarose/inorganic particles were washed with water to remove the ethanol.

The calculated density of the hybrid particles obtained in experiment 4 is 1.3 g/ml.

Experiment 5

Synthesis of Magnetic Porous Agarose/Inorganic Particles Hybrid Particles

A mixture of 3.7 g agarose, 30 g Kemira AFDC and 7 g magnetite disperged in 80 ml water was placed in a round bottom flask and heated in an oil bath (100° C.) for one hour (approximately 95° C. in the flask).

In parallel, a solution of 14 g ethyl cellulose in 200 ml toluene was prepared in a jacketed reactor. A circulation bath was connected to the reactor and set to a temperature of 60° C. An impeller was used to mix and solve the ethyl cellulose with the toluene.

When the temperature reached 60° C., the agarose/magnetite/inorganic slurry was added to the toluene phase in the reactor. The stirring rate was stepwise increased during emulsification and the emulsion was allowed to equilibrate for at least 5 min at each stirring rate. After each step a sample was withdrawn and the size of the agarose/magnetite/inorganic particles was estimated using an optical light microscope. When the mean particle diameter was estimated to less than 100 μm the emulsification process was stopped by cooling the reactor to 15° C. by adding ice to the circulation bath.

The obtained agarose/magnetite/inorganic particles were disperged in ethanol to remove ethyl cellulose and thereafter allowed to sediment. The supernatant was removed. This washing procedure was repeated 5 times. To see if the supernatant was removed after 5 washes, some of the supernatant was added to water. If there was a precipitation the ethyl cellulose was still present and the agarose/magnetite/inorganic hybrid particles were further washed with ethanol. Thereafter the agarose/inorganic particles were washed with distilled water to remove the ethanol.

The calculated density of the magnetic hybrid particles obtained in experiment 5 is 1.3 g/ml.

Experiment 6 A-C

A mixture of 18 g agarose, 100 g titanium dioxide (see Table 4) and 40 g magnetite dispersed in 400 ml water was placed in a round bottom flask and heated in an oil bath (100° C.) for one hour (approximately 95° C. in the flask).

TABLE 4

Properties of titanium dioxide used for Experiment 6.

| Exp. No | Supplier | Commerial name | Crystal phase | Size | Surface area |
|---|---|---|---|---|---|
| 6A | Kemira | Kemira AFDC | anatase | d50 0.6 μm measured by LALLS | ~10 m²/g |
| 6B | Sensient | 500095 Eurovit titanium dioxide | anatase | d50 0.65 measured by LALLS | — |
| 6C | Sigma-Aldrich | | anatase | <25 nm from supplier | spec. surface 200-220 m²/g from supplier |

In parallel, a solution of 68-90 g ethyl cellulose in 1500 ml toluene was prepared in a jacketed reactor. A circulation bath was connected to the reactor and set to a temperature of 60° C. Intermig stirrers were used to mix and solve the ethyl cellulose with the toluene.

When the temperature reached 60° C., the agarose/magnetite/inorganic slurry was added to the toluene phase in the reactor. The stirring rate was stepwise increased during emulsification and the emulsion was allowed to equilibrate for at least 10 min at each stirring rate. After each step a sample was withdrawn and the size of the agarose/magnetite/inorganic particles was measured (using Low Angle Laser Light Scattering). When the mean particle diameter was 62±5 μm the emulsification process was stopped by cooling the reactor to 15° C. by adding ice to the circulation bath.

The obtained agarose/magnetite/inorganic particles were dispersed in ethanol to remove ethyl cellulose and thereafter allowed to sediment. The supernatant was removed. This washing procedure was repeated 5 times. To see if the supernatant was removed after 5 washes, some of the supernatant was added to water. If there was a precipitation the ethyl cellulose was still present and the agarose/magnetite/inorganic hybrid particles were further washed with ethanol. Thereafter the agarose/inorganic particles were washed with distilled water to remove the ethanol.

The calculated density of the magnetic hybrid particles obtained in experiment 6 is 1.2 g/ml.

Experiment 7

Cross-Linking of Porous Agarose/Inorganic Hybrid Particles

A total volume of 0.12 l of the in Experiment 2 and Experiment 3 synthesized hybrid particles and distilled water was added to a three-necked round bottom flask. 14.9 g sodium sulphate, 0.10 g sodium borohydride and 1.05 ml sodium hydroxide (50%) were also added. The round bottom flask was placed in a preheated oil bath (47° C.). Epichlorohydrin was added with a dose speed of 0.034 ml/min using a Dosimat pump to a total volume of 12.4 ml. Sodium hydroxide (50%) was added with a dose speed of 0.024 ml/min using a Dosimat pump to a total volume of 8.5 ml. The reaction was left to proceed over night.

The next day the reaction mixture was neutralized by adding acetic acid, approximately 2.86 ml, until pH was 7. The cross-linked particles were washed on glass filter with plenty of distilled water. Finally, the hybrid particles were sieved through a 315 μm sieving cloth.

Experiment 8

Functional Tests of Hybrid Particles Prepared in Experiment 3-5

A model sample was used containing a tryptic digest of bovine serum albumin, BSA, spiked with a pure mono phos phopeptide (0.9 mass %) from β-casein with known molecular weight (2062 g/mol).

A functional test was performed to see if the inorganic particles were able to enrich β-casein. MALDI-TOF was used for qualitative evaluation of the sample after enrichment on the hybrid particles. The model sample was prepared with such low initial concentration of the phosphopeptide β-casein in the sample so that no signal at m/z 2062 was obtained from β-casein in the MALDI-TOF spectra before the enrichment step. Meaning that, if a peak with m/z 2062 was detected in the MALDI-spectrum enrichment was achieved. The enrichment was performed on a small scale using SPINTRAP™ columns The hybrid particles were loaded in the columns and thereafter the sample was applied. The following protocol was used in the functional test:

Protocol for Functional Test

1) Add 80 µl 50% media slurry to SPINTRAP™ column (use large pipette tip or cut the pipette tip). This gives 40 µl particles. Centrifuge 1 min 200×g.
2) Add 500 µl wash/equilibration buffer (DHB (20 mg/ml) in 80% ACN, 0.1% TFA). Vortex SPINTRAP™ column briefly. Centrifuge 1 min 200×g.
3) Mix 20 µl mono phosphate peptides dissolved in equilibration buffer (50 mM Glycin-HCL, 50% ACN) with 220 µl trypsinated BSA (2 mg/ml)
4) Add 240 µl wash/equilibration buffer (DHB (20 mg/ml) in 80% ACN, 0.1% TFA) to the sample mixture.
5) Add the diluted sample mixture to the SPINTRAP™ column Rotate end-over-end 90 min Centrifuge 1 min 200×g. Save flow through.
6) Add 500 µl wash/equilibration buffer (DHB (20 mg/ml) in 80% ACN, 0.1% TFA). Vortex SPINTRAP™ column briefly. Centrifuge 1 min 200×g. Save wash 1.
7) Add 500 µl wash/equilibration buffer (DHB (20 mg/ml) in 80% ACN, 0.1% TFA). Vortex SPINTRAP™ column briefly. Centrifuge 1 min 200×g. Save wash 2.
8) Add 500 µl wash buffer 50 mM Glycin-HCL, 50% ACN. Vortex SPINTRAP™ column briefly. Centrifuge 1 min 200×g. Save wash 3.
9) Add 500 µl wash buffer 50 mM Glycin-HCL, 50% ACN. Vortex SPINTRAP™ column briefly. Centrifuge 1 min 200×g. Save wash 4.
10) Elute sample by adding 500 µl elution buffer (1% Phosphoric acid, 50% ACN). Incubate 5 min with end-over-end rotation. Centrifuge 1 min 1000×g. Save eluate.
11) Store flow through, wash 1, wash 2, wash 3, wash 4 and eluate at −20° C.

Results of Functional Test

Results from the first try to enrich phosphopeptides, which was only washed with 80% ACN and 0.1% TFA, shows in a MALDI-spectrum that an enrichment of phosphopeptides was achieved. In a MALDI-spectrum of a spiked sample (i.e. a sample before enrichment), the peak that indicates the mono phosphopeptide at 2062 m/z could not be detected.

The agarose/inorganic particles were evaluated according to the above protocol in experiment 5. Table 5 describes how many peaks and the peak intensity for the mono phosphopeptide.

TABLE 5

Results from screening of agarose/inorganic particles.

| Exp. no | Inorganic particle | Number of detected peaks | Peak intensity for 2062 m/z (%) |
|---------|--------------------|--------------------------|----------------------------------|
| 3A | FINNTI X-141 | 12 | 100 |
| 3B | Kemira AFDC | 2 | 100 |
| 3C | UV-Titan MIII | 15 | 8 |
| 3D | VP TiO2 PV90 | 3 | 100 |
| 4 | Kemira AFDC | 2 | 100 |
| 5 | Kemira AFDC | 2 | 100 |

Screening of the agarose/inorganic particles showed excellent results (Table 5). For experiment 3B (Kemira AFDC) only two peaks were detected, the mono phosphopeptide with a peak intensity at 100% and a peak at 1992 m/z. This titanium dioxide was selected for the further evaluation in Experiments 4 and 5, and the same excellent result was obtained.

Experiment 9

Functional Test with More Complex Sample

The hybrid particles from Experiment 7 were further evaluated using a more complex sample containing tryptic peptides from a mixture of E. coli cell extract spiked with bovine β-casein (10%), chicken egg ovalbumin (5%) and creatin kinase from rabbit muscle (2.5%). According to annotations in the Swiss-Prot database and MS/MS analysis of pure proteins, there should be 2 phosphorylated tryptic peptides from beta-casein, 2 from ovalbumin and 1 from creatin kinase.

The peptide mix was purified using the porous hybrid particles and the eluates were evaporated to remove residual acetonitrile. The peptides remaining after purification with the hybrid particles produced according to the present invention were analyzed with LC-MS/MS (pepmap C-18 RPC column connected to an ion trap MS instrument via nanospray interface).

After enrichment and analysis with LC-MS/MS both beta-casein and ovalbumin were recovered, by detection of one phosphorylated peptide from each protein. The expected tryptic peptide from creatin kinase was not found by MS/MS. Some phosphorylated peptides give a prominent loss of phosphoric acid in MS/MS as a neutral loss without extensive fragmentation of the peptide backbone giving very poor MS/MS spectra that are not suitable for database searches. Several different MS methods need to be used to get a complete analysis of phosphorylated peptides.

Experiment 10

Functional Test of Hybrid Particles from Experiment 6A and 6B Sample Mixture

The sample mixture consisted of three phosphopeptides:
100 ng (59 pmol) Kinase Domain of Insulin Receptor-3, m/z 1702.7472
100 ng (48 pmol) Bovine β-Casein monophosphopeptide, m/z 2061.8284
1000 ng (460 pmol) PKA Regulatory Subunit II Substrate Calcineurin (PP2B) Substrate, m/z 2192.0859 spiked in 100 µg trypsin digested Bovine Serum Albumin (BSA). The sample was then diluted with equilibration/binding buffer to a total volume of 112 µl before applied on the hybrid particles.

Buffer System

The buffer systems used in testing hybrid particles from experiment 6A and 6B are listed in Table 6.

TABLE 6

Buffer system used in functional test of hybrid particles from experiment 6A and 6B

| Equilibration/Binding | Wash 1 | Wash 2 | Wash 3 | Elution |
|---|---|---|---|---|
| 1M Glycolic acid in 80% ACN, 5% TFA, pH 2 | 1M Glycolic acid in 80% ACN, 5% TFA, pH 2 | 1M Glycolic acid in 80% ACN, 5% TFA, pH 2 | 80% ACN, 1% TFA, pH 1 | 10% $H_3PO_4$/ 50% ACN |

Protocol for Functional Testing 1.5 ml micro centrifuge tubes were used together with a magnetic rack. The magnet was removed before buffer and sample application.

1. Add 20 µl 50% media slurry into a micro tube. Gives 10 µl media.
2. Add 500 µl binding/equilibration buffer, mix a few times and throw away buffer.
3. Add the diluted sample mixture. Rotate end-over-end 30 min. Throw away flow trough.
4. Add 500 µl wash buffer 1, mix a few times and throw away buffer.
5. Add 500 µl wash buffer 2, mix a few times and throw away buffer.
6. Add 500 µl wash buffer 3, mix a few times and throw away buffer.
7. Elute sample by adding 20 µl elution buffer. Incubate 5 min with end-over-end. Repeat once. Save eluates. Start material and eluates were analyzed with MALDI-TOF.

Results

The results from the functional testing of hybrid particles from experiment 6A and 6B showed enrichment of phosphopeptides (Table 7).

TABLE 7

Results from functional testing of hybrid particles from experiment 6A and 6B

| Exp | No peaks starting material | No of peaks 1$^{st}$ eluate | | No of peaks 2$^{nd}$ eluate | |
|---|---|---|---|---|---|
| | | Non-phosphorylated | Phosphorylated | Non-phosphorylated | Phosphorylated |
| 6A | 40 | 5 | 3 | 10 | 3 |
| 6B | 40 | 6 | 3 | 3 | 3 |

Experiment 11

Functional Test of Hybrid Particles from Experiment 6C

Sample Mixture

The sample mixture consisted of three phosphopeptides:
- 1000 ng (590 pmol) Kinase Domain of Insulin Receptor-3, m/z 1702.7472
- 1000 ng (480 pmol) Bovine β-Casein monophosphopeptide, m/z 2061.8284
- 1000 ng (460 pmol) PKA Regulatory Subunit II Substrate Calcineurin (PP2B) Substrate, m/z 2192.0859 spiked in 100 µg trypsin digested Bovine Serum Albumin (BSA). The sample was then diluted with equilibration/binding buffer to a total volume of 145 µl before applied on the hybrid particles.

Buffer System

The buffer systems used in testing hybrid particles from experiment 6C are listed in Table 8.

TABLE 8

Buffer system used in functional test of hybrid particles from experiment 6C

| Equilibration/Binding | Wash 1 | Wash 2 | Elution |
|---|---|---|---|
| 1M Glycolic acid in 80% ACN, 5% TFA | 1M Glycolic acid in 80% ACN, 5% TFA | 80% ACN, 1% TFA | 10% $H_3PO_4$, 50% ACN |

Protocol for Functional Testing 1.5 ml micro centrifuge tubes were used together with a magnetic rack. The magnet was removed before buffer and sample application.

1) Add 20 µl 50% media slurry into a micro tube. Gives 10 µl media.
2) Add 500 µl binding/equilibration buffer.
3) Add the diluted sample mixture, 145 µl. Rotate end-over-end 30 min Throw away flow through.
4) Add 500 µl wash buffer 1, mix a few times and throw away buffer.
5) Add 500 µl wash buffer 2, mix a few times and throw away buffer.
6) Elute sample by adding 50 µl elution buffer. Incubate 5 min with end-over-end rotation. Repeat once. Save eluates.

Start material and eluates were analyzed using MALDI-TOF.

Results

Starting material showed 27 detected peaks. All 3 phospho peptides were detected after enrichment. Total number of peaks in 1$^{st}$ eluate was 12. Total number of peaks in 2$^{nd}$ eluate was 9.

While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for production of separation media for separation of biomolecules from a sample, comprising the following steps: addition of inorganic metal oxide particles selected from Group 4, 12, 13 and 14, to an organic solution to form a mixture; and emulsification of said mixture to form porous hybrid particles,
wherein each porous hybrid particle contains a plurality of inorganic metal oxide particles, and wherein the density of said porous hybrid particles is between 1.0 and 1.5g/ml, and wherein said inorganic particles have a shape and size that maximizes their active surface area accessible within the hybrid porous particles for interaction with biomolecules, wherein the inorganic metal oxide particles are less than 1000 nm in size.

2. The method of claim 1, wherein the inorganic metal oxide particles are porous.

3. The method of claim 1, wherein the inorganic metal oxide particles are less than 300 nm in size.

4. The method of claim 1, wherein the inorganic metal oxide particles are selected from the group consisting of titania, zirconia, hafnia, alumina, zinkoxide, germania and tin dioxide.

5. The method of claim 1, wherein the organic solution comprises polysaccharides.

6. The method of claim 5, wherein the organic solution comprises agarose and said inorganic metal oxide particles comprise titania.

7. The method of claim 5, wherein the polysaccharides are selected from the group consisting of agarose and dextran.

8. The method of claim 1, wherein the organic solution comprises synthetic material.

9. The method of claim 8, wherein the synthetic material is selected from the group consisting of (i) polystyrene/dvb and porogens, and (ii) methacrylates and porogens.

10. The method of claim 1, wherein magnetic particles are incorporated into said organic solution.

11. The method of claim 1, wherein the density of the porous hybrid particles is between 1.0 and 1.3 g/ml.

12. The method of claim 1, wherein the inorganic metal oxide particles are selected from the group consisting of titania, zirconia and alumina.

13. The method of claim 1, wherein the inorganic metal oxide particles are titania.

14. Porous hybrid particles comprising inorganic metal oxide particles selected from Group 4, 12, 13 and/or 14 which are incorporated in an organic solution to form porous hybrid particles, wherein each porous hybrid particle contains a plurality of inorganic metal oxide particles, wherein the density of the porous hybrid particles is between 1.0 and 1.5 g/ml, and wherein said inorganic particles have a shape and size that maximizes their active surface area accessible within the porous hybrid particles for interaction with biomolecules, wherein the inorganic metal oxide particles have a (volume-weighted, sphere volume-equivalent) average diameter less than 1000 nm.

15. The porous hybrid particles of claim 14, wherein the inorganic metal oxide particles have a (volume-weighted, sphere volume-equivalent) average diameter less than 300 nm.

16. The porous hybrid particles of claim 14, wherein the inorganic particles are selected from the group consisting of titania, zirconia, hafnia, alumina, zinc oxide, germania and tin dioxide.

17. The porous hybrid particles of claim 14, wherein the organic solution is selected from polysaccharides or synthetic polymers.

18. The porous hybrid particles of claim 14, wherein said inorganic particles comprise titania and the organic solution comprises agarose.

19. The porous hybrid particles of claim 14, comprising a lid covering the hybrid particles, wherein said lid comprises up to 20% agarose.

20. The porous hybrid particles of claim 14, wherein magnetic particles are incorporated into said organic solution.

21. The porous hybrid particles of claim 14, wherein the size of the particles is 5-500 μm.

22. The porous hybrid particles of claim 14, wherein the density of the porous hybrid particles is between 1.0 and 1.3 g/ml.

23. The porous hybrid particles of claim 14, wherein the inorganic metal oxide particles are selected from the group consisting of titania, zirconia and alumina.

24. The porous hybrid particles of claim 14, wherein the inorganic metal oxide particles are titania.

25. The porous hybrid particles of claim 14, wherein the size of the particles is 25-100 μm.

* * * * *